United States Patent [19]

Aktogu et al.

[11] Patent Number: 4,904,655
[45] Date of Patent: Feb. 27, 1990

[54] NOVEL INDOLO [3,2,1-DE] [1,4] OXAZINO [2,3,4-IJ] [1,5]

[75] Inventors: Nurgün Aktogu, Le Plessis Robinson; Francoise Delevallee, Fontenay Sous Bois; François Clemence; Claude Oberlander, both of Paris, all of France

[73] Assignee: Roussel Uclaf, Paris, France

[21] Appl. No.: 302,810

[22] Filed: Jan. 26, 1989

[30] Foreign Application Priority Data

Jan. 26, 1988 [FR] France .................. 88 00840

[51] Int. Cl.[4] .................. C07D 413/04; A61K 31/435
[52] U.S. Cl. ..................................... 514/229.5; 544/99
[58] Field of Search ......................... 544/99; 514/229.5

[56] References Cited

U.S. PATENT DOCUMENTS 4,493,836 1/1985 Nedelec et al. .................. 544/99

FOREIGN PATENT DOCUMENTS 2383182 4/1978 France .

Primary Examiner—Mukund J. Shah
Assistant Examiner—C. L. Cseh
Attorney, Agent, or Firm—Bierman & Muserlian

[57] ABSTRACT

Novel compounds selected from the group consisting of all possible racemic or optically active forms of compounds of the formula wherein $R_1$ and $R_2$ are individually selected from the group consisting of hydrogen, alkyl and alkoxy of 1 to 5 carbon atoms, -OH, -$CF_3$ and -$NO_2$ and is selected from the group consisting of and their non-toxic, pharmaceutically acceptable acid addition salts having a very good analgesic activity as well as antidepressive, neuronal protective, anti-anoxic, anti-ischemic and no-otropic activities.

21 Claims, No Drawings

NOVEL INDOLO [3,2,1-DE] [1,4] OXAZINO [2,3,4-IJ] [1,5]

STATE OF THE ART

Related prior art includes French Pat. No. 2,383,182 and U.S. patent applications Ser. No. 271,733 filed Nov. 15, 1988 and via PCT Ser. No. 8800562 filed Nov. 16, 1988 corresponding to application number BF 87 15980.

OBJECTS OF THE INVENTION

It is an object of the invention to provide the novel compounds of formula I and their non-toxic, pharmaceutically acceptable acid addition salts and a novel process and intermediates for their preparation.

It is another object of the invention to provide novel analgesic compositions and a novel method of relieving pain in warm-blooded animals.

These and other objects and advantages of the invention will become obvious from the following detailed description.

THE INVENTION

The novel compounds of the invention are selected from the group consisting of all possible racemic or optically active forms of compounds of the formula

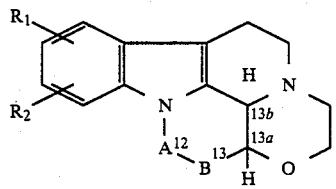

wherein $R_1$ and $R_2$ are individually selected from the group consisting of hydrogen, halogen, alkyl and alkoxy of 1 to 5 carbon atoms, -OH, -CF$_3$ and -NO$_2$ and

is selected from the group consisting of

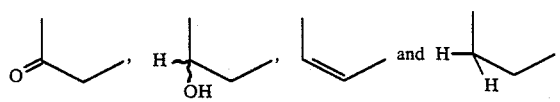

and their non-toxic, pharmaceutically acceptable acid addition salts.

In the products of formula I, the hydrogen atom in position 13b and the hydrogen atom in position 13a can each occupy one or the other of the α- and β- orientations which determines the existence of cis and trans diastereo isomers. Similarly, the hydroxy radical in position 12 can have the α- or β- form.

Examples of $R_1$ and $R_2$ as alkyl or alkoxy are methyl, ethyl, n-propyl, isopropyl, n-butyl, isobutyl, n-pentyl, methoxy, ethoxy, n-propoxy, isopropoxy and branched or linear butoxy. Preferably, $R_1$ and $R_2$ are alkyl of 1 to 3 carbon atoms or alkoxy of 1 to 2 carbon atoms. When $R_1$ and/or $R_2$ is halogen they are preferably chlorine but they may be fluorine, bromine or iodine.

Examples of suitable acids for the formation of the non-toxic, pharmaceutically acceptable acid addition salts are inorganic acids such as hydrochloric acid, hydrobromic acid, hydriodic acid, nitric acid, sulfuric acid, phosphoric acid, organic acids such as propionic acid, acetic acid, formic acid, benzoic acid, maleic acid, fumaric acid, succinic acid, tartaric acid, citric acid, oxalic acid, glyoxylic acid, aspartic acid and ascorbic acid; alkane-monosulfonic acids such as methanesulfonic acid, ethanesulfonic acid and propanesulfonic acid; alkanedisulfonic acids such as methanedisulfonic acid and α,β-ethanedisulfonic acid, arylmonosulfonic acids such as benzenesulfonic acid and the aryldisulfonic acids.

Among the preferred compounds of formula I are all possible racemic and optically active isomeric forms of the compounds wherein $R_1$ and $R_2$ are individually selected from the group consisting of hydrogen, methyl, ethyl, methoxy, ethoxy, chlorine, -OH, -CF$_3$ and -NO$_2$ and those wherein

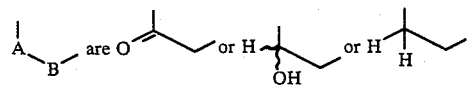

and their acid addition salts.

Specific preferred compounds of formula I are [12RS (12 13a α, 13b β)](±) 2,3,5,6,12,13,13a,13b-octahydro indolo [3,2,1-de] [1,4] oxazino [2,3,4,-ij] [1,5] naphthyridin-12-ol, [12RS (12α, 13a β, 13b α)] (±) 2,3,5,6,12,13,13a,13b-octahydro indolo [3,2,1-de] [1,4] oxazino [2,3,4-ij] [1,5] naphthyridin -12-ol, (13aRS-trans) (±) 2,3,5,6,12,13,13a,13b-octahydro indolo [3,2,1-de] [1,4] oxazino [2,3,4,-ij] [1,5] naphthyridine, (13aRS-cis) (±) 2,3,5,6,13a,13b-hexahydro indolo [3,2,1-de] [1,4] oxazino [2,3,4-ij] [1,5] naphthyridin-12-(13H)-one and their addition salts with mineral or organic acids.

The novel process of the invention for the preparation of the compounds of formula I comprises reacting a compound of the formula

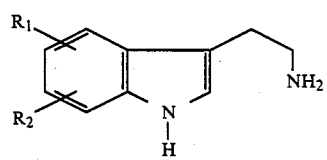

wherein $R_1$ and $R_2$ have the above definitions with a compound of the formula

X-CH$_2$-COOR wherein X is halogen and R is alkyl of 1 to 2 carbon atoms to obtain a compound of the formula

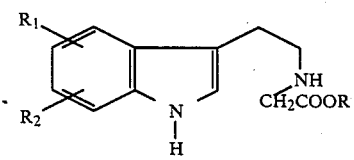

reducing the latter to obtain a compound of the formula

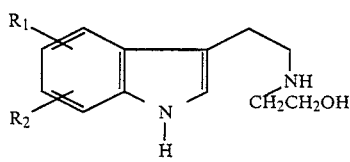

condensing the latter either with a maleic anhydride to obtain a product of the formula

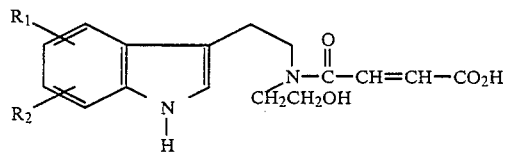

and esterifying the latter to obtain a product of the formula

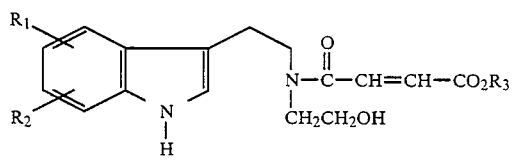

wherein $R_3$ is alkyl of 1 to 2 carbon atoms, or with an acid chloride of the formula

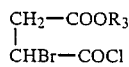

wherein $R_3$ is defined as above to obtain a mixture of the product of formula $V_A$ and of a product of the formula

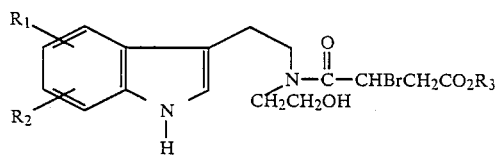

cyclizing the products of formula $V_A$ and VII to obtain a product of the formula

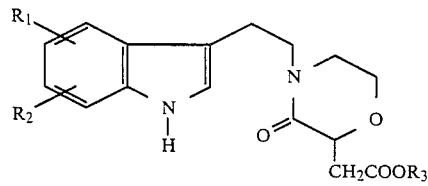

reacting the latter with phosphorus oxychloride to obtain the product of the formula

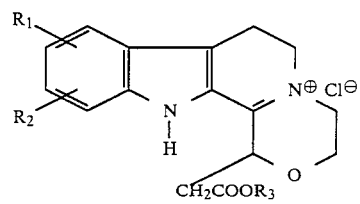

and either converting the latter to the perchlorate of the formula

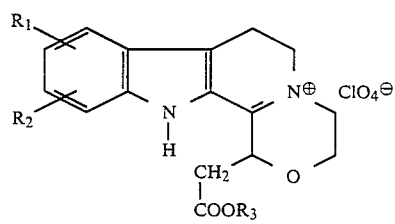

and either reducing the compound of formula $IX_2$ to the compound of the formula X in which the two hydrogen atoms in positions 13b and 13a are in position cis:

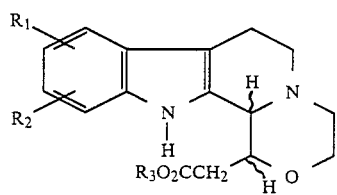

and then cyclizing the latter in an acid medium to obtain a compound of the formula $IA_1$ corresponding to a product of formula I in which

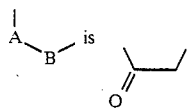

and the two hydrogen atoms in positions 13b and 13a are in position cis, or the compound of formula $IX_2$ is cyclized in an acid medium to a compound of the formula

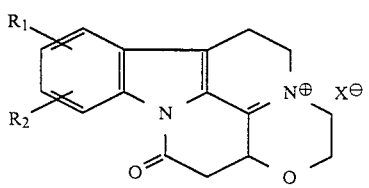

$X\ominus$ being the anion from the acid used, and reducing the latter to obtain a compound of formula $IA_2$ corresponding to a product of formula I in which

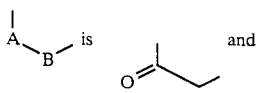

and the two hydrogen atoms in positions 13b and 13a are in position trans or the product of formula IX$_1$ is cyclized in an acid or basic medium to obtain a product of the formula

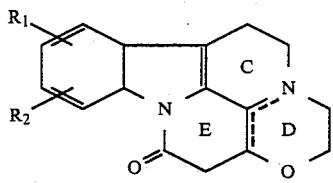

XII wherein the dotted line is double bond between the rings C and D or between the rings D and E and reducing the latter to obtain a product of formula IA$_2$ as defined previously, the said compound of formula IA$_1$ and IA$_2$ being optionally reduced to compounds corresponding to formulae IB$_1$ and IB$_2$ corresponding to compounds of formula I in which

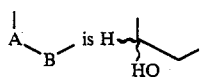

the said compounds of formulae IB$_1$ and IB$_2$ being optionally dehydrated to obtain compounds corresponding to formula IC$_1$ and IC$_2$ corresponding to compounds of formula I in which

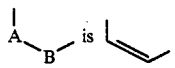

the said compounds of formulae IC$_1$ and IC$_2$ being optionally reduced to compounds of formulae ID$_1$ and ID$_2$ corresponding to compounds of formula I in which

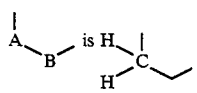

and optionally the products of formula I obtained by the action of a mineral or organic acid are salified.

In a preferential mode of the processing, the compound reacting with the compound of formula II is ethyl bromoacetate with the reaction being carried out in the presence of a base such as triethylamine or potassium carbonate and the reduction of the compound of formula III to a compound of formula IV is carried out with a mixed hydride such as, for example, the mixed lithium and aluminum hydride, sodium and aluminium diethylhydride, boron and lithium triethylhydride. The reaction of the compound of formula IV with maleic anhydride or with the compound of formula VI is carried out by phase transfer with a solvent such as chloroform or a benzene-acetonitrile mixture being used as the organic phase. The reaction is carried out in the presence of a base such as potassium carbonate and a phase-transfer agent, notably bromide or hydrogensulfonate of tetrabutyl-ammonium.

R$_3$ is preferably methyl in the compound of formula V$_A$ and in the compound of formula VI. The esterification of the compound of formula V to a compound of formula V$_A$ is carried out with an ion-exchange resin in methanol at reflux and the cyclization of the compounds of formula V$_A$ and VII to the compound of formula VIII is carried out in the presence of potassium carbonate. The perchlorate of formula IX$_2$ is obtained by reaction of perchloric acid in an aqueous medium. The reduction of the compound of formula IX$_2$ to the compound of formula X is carried out with sodium borohydride.

The cyclization of the compound of formula X to the compound of formula IA$_1$ is carried out in the presence of hydrochloric acid and the cyclization of the compound of formula IX$_2$ to the immonium salt of formula XI is carried out with hydrochloric acid or hydriodic acid. The cyclization of the compound of formula IX$_1$ is carried out either under conditions as those described previously leading to the compound of formula XI and in which case the double bond is situated between the rings C and D, or using a base, for example ammonia in the presence of an anti-oxidizing agent such as ascorbic acid, and in which case the double bond is situated between the rings D and E.

The reduction of the compounds of formulae XI and XII to a compound of formula IA$_2$ is carried out with sodium borohydride in the presence of acetic acid. The reduction of compounds of formula I$_A$ in which

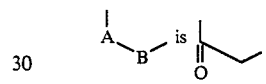

to compound of formula I$_B$ in which

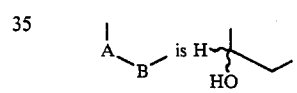

is carried out with a hydride, notably a mixed hydride such as for example mixed lithium and aluminium hydride, or sodium and aluminium diethylhydride. The dehydration agent used to obtain from compounds of formula I$_B$ in which

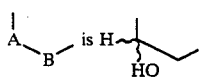

compounds of formula I$_C$ in which

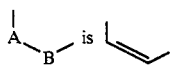

is an acid such as hydrochloric acid, hydrobromic acid, sulfuric acid, acetic acid, p-toluenesulfonic acid or methanesulfonic acid in catalytic quantities. The reduction agent to which the compounds of formula I$_C$ in which

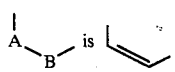

are submitted to obtain compounds of formula I$_D$ in which

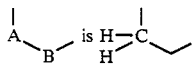

is hydrogen in the presence of a catalyst such as platinium or palladium. The optically active forms of products of formula I can be prepared by resolving the racemate following the usual methods.

The analgesic compositions of the invention are comprised of an analgesically effective amount of at least one compound of formula I and their non-toxic, pharmaceutically acceptable acid addition salts and an inert pharmaceutical carrier or excipient. The compositions may be in the form of tablets, dragees, gelules, ointments, creams, gels, aerosol preparations and injectable solutions or suspensions.

Examples of suitable excipients are talcum, gum arabic, lactose, starch, magnesium stearate, cocoa butter, aqueous or non-aqueous vehicles, fatty substances of animal or vegetable origin, paraffin derivatives, glycols, various wetting, dispersing and emulsifying agents and preservatives.

The analgesic compositions are useful for the treatment of muscular, articulatory or nervous pains, toothaches, migraines shingles and equally as complementary treatment of infectious and febrile states.

The compounds of formula I also show interesting anti-depressve, nootropic (notably anti-amnesic), neuronal protective, anti-anoxic and anti-ischemic properties and they can also be used in the treatment of cerebral deficiencies of anoxic or ischemic origin, disorders of memory and attention. They can also be used as anti-depressants.

The novel method of the invention of relieving pain in warm-blooded animals, including humans, comprises administering to warm-blooded animals analgesically effective amount of at least one compound of formula I and their non-toxic, pharmaceutically acceptable acid addition salts. The compounds may be administered orally, rectally, parenterally or topically to the skin or mucous membranes. The usual daily dose is 0.13 mg to 26.6 mg mg/kg depending on the condition treated, the specific compound used and the method of administration.

The novel intermediates of the invention are the compounds of formulae III, IV, V, VA, VII, VIII, $IX_1$, $IX_2$, X and XII and the acid chlorides of formula VI which are prepared by chlorination of the corresponding acids.

In the following examples there are described several preferred embodiments to illustrate the invention. However, it is to be understood that the invention is not intended to be limited to the specific embodiments.

EXAMPLE 1

(cis dl) (13aRS-cis) (±) 2,3,5,6,13a,13b-hexahydro indolo [3,2,1-de] [1,4] oxazino [2,3,4-ij] [1,5] naphthyridin-12 (13H)-one hydrochloride STEP A: Ethyl [[2-(1H-indol-3-yl)-ethyl]-amino]-acetate A mixture of 500 g of tryptamine in 11 liters of methylene chloride was stirred for one hour and then 512 g of potassium carbonate in 1540 ml of water were added all at once followed by 360 ml of ethyl bromoacetate added all at once. The reacton mixture was vigorously stirred for 20 hours and after decanting, the aqueous phase was extracted with methylene chloride. The organic phase was washed with water, and the aqueous phase was extracted again with methylene chloride. The combined organic phase were dried and evaporated to dryness at 40° C. under 20 mm of pressure. The residue was chromatographed on silica and eluted first with a methylene chloride - ethyl acetate mixture (8-2) to obtain 155.3 g of diester, then with pure ethyl acetate to obtain 398.5 g of the expected product which was used as is for the next step.

STEP B: 2-[[2-(1H-indol-3-yl)-ethyl]-amino]-ethanol 398 g of the product of Step A were dissolved in 4 liters of tetrahydrofuran cooled to +10° C. and while maintaining this temperature, 400 g of 25% sodium diethyl dihydroaluminate in toluene were introduced. The mixture was stirred for 90 minutes while allowing the temperture to rise to 17° C. The medium was cooled to −10° C. and 400 ml of sodium hydroxide solution in 1200 ml of water were introduced over 80 minutes while keeping the temperature at 0° C. during the introduction. The mixture was stirred for 2 hours at +10° C. then allowed to rise to ambient temperature for 16 hours with slower stirring. After decanting, the organic phase was washed with water and the wash water was extracted with ethyl acetate and methylene chloride. The combined organic phases were diluted with methylene chloride and dried, and the solvents were expelled at 40° C. under reduced pressure. The residue was triturated in 1300 ml of ethyl acetate for one hour, separated, washed with ethyl acetate and dried to obtain 240.8 g of the expected product melting at 92° C.

STEP C: Methyl [4-[2-(1H-indol-3-yl)-ethyl]-3-oxo-2-morpholin-yl]-acetate 4.08 g of the product of Step B were suspended in 90 ml of a benzene - acetonitrile mixture (2-1) and then 5.5 g of potassium carbonate in 30 ml of water were added followed by 0.4 g of tetrabutylammonium bromide. The mixture was strongly stirred while adding 1.930 g of maleic anhydride and was refluxed for 24 hours under strong stirring. After cooling, the medium was acidified with a solution of 2N hydrochloric acid to a pH of 3–4 and the two phases were decanted. The aqueous solution was reextracted with a chloroform - methanol mixture (8-2) and the combined organic solutions were dried and concentrated to dryness to obtain 6.1 g of the product. 4.5 g of the latter were dissolved in 90 ml of methanol and after 4.5 g of ion-exchange resin were added, the mixture was refluxed for 20 hours After cooling, the resin was filtered off and washed with methanol. The filtrate and the washings were concentrated under reduced pressure to obtain 3.4 g of oily product. 1.7 g of the latter were dissolved in 34 ml of tetrahydrofuran and 1.7 g of potassium carbonate were added. The mixture was refluxed under an inert atmosphere for 16 hours and then was filtered and washed with ethyl acetate. The filtrate was concentrated to dryness to obtain 0.900 g of the expected product melting at 144° C.

STEP D: Perchlorate of 1-(2-methoxy-2-oxoethyl)-1,3,4,6,7,12-hexahydro [1,4] oxazino [4',3'-1,2] pyrido [3,4-b] indol-5-ium 5 g of the product of Step C were suspended in 50 ml of phosphorus oxychloride and the mixture was refluxed for 3 hours, then concentrated to about 25 ml. The mixture was poured slowly over 15 minutes into 250 ml of ice and water containing 25 ml of 65% perchloric acid. The mixture was stirred for one hour at 0° C., then separated, washed with water and dried under reduced pressure at 30° C. to obtain 5.5 g of the expected product which was used as is for the next step.

STEP E: Methyl (1R,cis) (±) 3,4,5,6,11,11b-hexahydro-1H-[1,4] oxazino [4',3',1,2] pyrido [3,4-b] indol-1-acetate The moist perchlorate was dissolved in 300 ml of methanol tetrahyduran mixture (1-1) cooled to 5° C. to 10° C., and 3.6 g of sodium borohydride were added over 15 minutes followed by stirring for one hour. The mixture was concentrated to dryness under reduced pressure. The residue was triturated in 150 ml of water for 30 minutes, separated, washed with water and taken up in 300 ml of a chloroform - methanol mixture (2-1). The insoluble part was filtered off and the filtrate was concentrated to dryness. The residue was crystallized from methanol and the 2.70 g of product were chromatographed on silica. Elution with a methylene chloride - methanol mixture (9-1) yielded 2.35 g of the expected product which after crystallization from methanol melted at 207° C.

STEP F: (cis dl) (13aRS cis) (±) 2,3,5,6,13a,13b-hexahydro indolo [3,2,1-de] [1,4] oxazino [2,3,4-ij] [1,5] naphthyridin-12 (13H)-one hydrochloride 8.9 g of the product of Step E were suspended in 89 ml of 5N hydrochloric acid and the mixture was refluxed for 3 hours, then cooled to 0° C. to −5° C., and brought to an alkaline pH by the addition of concentrated ammonia. The mixture was stirred for one hour at 0° C. to −5° C. and after separating, washing with water and drying under reduced pressure at 60° C., 7.5 g of product melting at 205° C. were obtained. 5 g of the product were partially dissolved at reflux in 125 ml of ethanol and 1.7 ml of concentrated hydrochloric acid were added hot. The solution was treated with active carbon, filtered, cooled to 0° C. and the hydrochloride was filtered off, and crystallized without drying from 200 ml of methanol to obtain 3.94 g of expected product.

NMR Spectrum, 250 MMz, ppm 3.66–3.78: H in position 2, 4.08–4.16: H in position 13a–13b, 2.43–2.70: H in position 5, 2.54–2.90: H in position 6, 2.96: H in position 13, 7.44–8.38: H in positions 7 and 10, 7.30: H in positions 8 and 9.

EXAMPLE 2

(trans dl) (13aRS, trans) (±)2,3,5,6,13a,13b-hexahydro indolo [3,2,1-de] [1,4] oxazino [2,3,4-ij] [1,5] naphthyridin-12 (13H)-one hydrochloride STEP A: 3,5,6,12,13,13a-hexahydro 12-oxo 2H-indolo [3,2,1-de] [1,4] oxazino [2,3,4-ij] naphthyridin-4-ium chloride 4.4 g of perchlorate of 1-(2-methoxy-2-oxoethyl) 1,3,4,6,7,12-hexahydro [1,4] oxazino [4',3'-1,2] pyrido [4,4-b] indol-5-ium were suspended in 38 ml of 5N hydrochloric acid and the suspension was heated to 100° C. for 16 hours. The reaction mixture was cooled to 0° C. for 30 minutes and the salt was filtered off, washed with water, dried and used as is for the next step.

STEP B: (trans dl) (13aRS, trans) (±) 2,3,5,6,13a,13b-hexahydro indolo [3,2,1-de] [1,4] oxazino [2,3,4-ij] [1,5] naphthyridin-12 (13H)-one hydrochloride The still moist salt of Step A was partially dissolved in 100 ml of acetic acid cooled to 10° C. and 3 g of sodium borohydride were added over 25 minutes which maintaining the temperature at less than 20° C. The mixture was stirred for one hour and then the acetic acid was distilled off. The residue was taken up with 150 ml of water cooled to 0° C. to 5° C. and was alkalized over 30 minutes with concentrated ammonia. The mixture was stirred for one hour at 0° C. to 5° C., separated, washed with water and dried under reduced pressure at 70° C. The product was chromatographed on silica and elution with a methylene chlorde - methanol mixture (9-1) yielded 7 g of product in the form of a base. 2 g of this product were crystallized from methanol and the product obtained was dissolved at reflux in 70 ml of methanol. 1 ml of concentrated hydrochloric acid was added and the mixture was stirred for 30 minutes at 0° C. to 5° C., separated, washed and dried under reduced pressure at 50° C. to obtain 1.90 g of the expected product melting at 230° C.

NMR Spectrum, 250 MHz $CDCl_3$ ppm, 3.73 (d,d,d J=5.9–11.5): trans junction CH-O, 3.92 to 4.10: $CH_2O$, 7.25 to 7.35: aromatic (2H), 7.42 (m): (1H), 8.32 (m): (1H), 2.63 to 3.22: (9H) other protons.

EXAMPLE 3

(cis dl) [12RS (12α,13aα,13b α)] (±) 2,3,5,6,12,13,13a,13b-octahydro indolo [3,2,1-de] [1,4] oxazino [2,3,4-ij] [1,5] naphthyridin-12-ol 8 g of the hydrochloride of (13aRS,cis) (±) 2,3,5,6,13a,13b-hexahydro indolo [3,2,1-de] [1,4] oxazino [2,3,4-ij] [1,5] naphthyridin-12 (13H)-one were dissolved in 400 ml of tetrahydrofuran cooled to 0° C. to 5° C. under an inert atmosphere and 23.5 ml of a toluene solution of diethyl-aluminum-sodium dihydride (titrated at 0.236M % ml) were added. The mixture was stirred for one hour under the above conditions. While being maintained at 0° C. to 5° C., the medium was hydrolyzed with 200 ml of tetrahydrofuran with 25% of water. Then 100 ml of water and 100 ml of ethyl acetate were added. After decanting, the aqueous phase was extracted with 100 ml of ethyl acetate and washed with water. The wash waters were extracted with ethyl acetate and the combined organic phases were dried and concentrated to dryness. The residue was chromatographed over silica and elution with a methylene chloride - methanol mixture (9-1) yielded 2.2 g of product with axial OH and 4.1 g of product with equatorial OH. The latter was crystallized from isopropanol to obtain the expected product melting at 206° C.

NMR Spectrum 250 MHz $CDCl_3$ ppm, 5.58: H in position 12, 3.84 to 3.95: H in the 13a and 13b cis position, 3.51 to 3.68: H in position 2, 2.30: H in position 3, 3.25: H in position 6, 1.73: H in position 13, 7.17–7.48–7.74: aromatic, 2.5 to 3.1: other protons.

EXAMPLE 4

(cis dl) [12RS] [12 α, 13a β, 13b β)] (±) 2,3,5,6,12,13,13a,13b-octahydro indolo [3,2,1-de] [1,4] oxazino [2,3,4-ij] [1,5] naphthyridin-12-ol Using the procedure of Example 3, 2 epimers were obtained namely 2.2 g with axial OH and 4.1 g with equatorial OH. The epimer with axial OH was crystallized from isopropanol at reflux to obtain 1.5 g of expected product melting at 180° C.

NMR Spectrum 250 MHz CDCl$_3$ ppm, 4.09 to 4.25: H in the 13a and 13b cis positions, 5.92: equatorial H in position 12, 3.79: axial OH, 3.67 to 3.83: H in position 2, 2.46 to 2.80: H in position 3, 3.35: H in position 6, 7.51: (2H), 7.1 to 7.25: aromatic 2H, 3.00: (1H), 2.65: (2H) other protons.

EXAMPLE 5

(trans dl) [12RS (12α, 13a β, 13bα)] (±) 2,3,5,6,12,13,13a,13b-octahydro indolo [3,2,1-de] [1,4] oxazino [2,3,4-ij] [1,5] naphthyridin-12-ol 0.8 g of [13aRS,trans] (±) 2,3,5,6,13a,13b-hexahydro indolo [3,2,1-de] [1,4] oxazino [2,3,4-ij] [1,5] naphthyridin-12 (13H)-one were dissolved in 20 ml of anhydrous tetrahydrofuran and the mixture was cooled to −70° C. under an inert atmosphere. 2.55 ml of a toluene solution of diethyl-aluminum-sodium dihydride titered at 23.6% were introduced over 15 minutes followed by stirring for one hour under these conditions. At −20° C., the reaction medium was hydrolyzed with 10 ml of tetrahydrofuran with 25% of water. After decanting, the aqueous phase was extracted with ethyl acetate and the combined organic phases were washed with water to a neutral pH, dried and concentrated to dryness under reduced pressure. The residue was crystallized from 60 ml of isopropanol at reflux to obtain 0.600 g of a mixture of 95% of product with equatorial OH and 5% of epimer with axial OH. After a second crystallization, the expected equatorial OH product melting at 225° C. and with a Rf=0.47 (acetone - CH$_2$Cl$_2$ formation 1-1 for product at Rf=0.35 axial OH) was obtained.

NMR Spectrum 250 MHz CDCl$_3$ ppm, 5.63 (dt J=5.5 and 9): H in position 12, 6.68 (d, J=9): OH, 7.0 to 7.15: indole H$_5$ and H$_6$, 7.39 to 7.65: H$_4$ and H$_7$ indole, 1.9 to 4.0: other protons.

EXAMPLE 6

(trans dl) [12RS [12α, 13aα, 13bβ)] (±) 2,3,5,6,12,13,13a,13b-octahydro indolo [3,2,1-de] [1,4] oxazino [2,3,4-ij] [1,5] naphthyridin-12-ol Using the procedure of Example 4, 9 g of a mixture of epimers were obtained (axial and equatorial OH)·3 g of the mixture were suspended in 30 ml of 2N hydrochloric acid, and heated for 48 hours at 40° C., then cooled and neutralized with 6 ml of concentrated ammonia. After separating and crystallizing from 200 ml of methanol, 1.5 g of axial OH epimer melting at 250° C. were obtained, 1 g of the expected product was recovered from the mother liquors and had a Rf=0.35 (CH$_2$Cl$_2$ - acetone formation 1-1).

NMR Spectrum 250 MHz DMSO ppm, 6.05 (m): H in position 12, 6.40 (d, J=6.5): axial OH, 7.01 (dt) 7.08 (dt): indole H$_5$-H$_6$, 7.38 (dd) 7.45 (dd): indole H$_4$-H$_7$, 3.95 (dd): H in position 2 (equatorial), 3.77 (m): H in position 2 (axial) and H of junction, in position 13a, 2.65 to 3.1: other protons.

EXAMPLE 7

[13aRS,cis] (±) 2,3,5,6,13a,13b-hexahydro indolo [3,2,1-de] [1,4] oxazino [2,3,4-ij] [1,5] naphthyridine hemifumarate 4.1 g of the mixture of the 2 hydroxylated epimers of Example 3 were suspended in 40 ml of toluene and the mixture was heated to 80° C. to dissolve the product. 0.2 g of p-toluene-sulfonic acid were introduced and the mixture was refluxed for 16 hours, cooled and filtered. The organic phase was washed with 20 ml of half-diluted concentrated ammonia, then with 20 ml of water. The wash waters were extracted with toluene and the combined organic phases were dried and concentrated to dryness. The residue was triturated in 20 ml of isopropyl ether, separated and dried under reduced pressure at 50° C. to obtain 3 g of the product melting at 148° C. 2 g of this product were dissolved in 30 ml of ethyl acetate at reflux and a boiling solution of 0.465 g of fumaric acid in 15 ml of isopropanol was added all at once. The mixture was stirred for 30 minutes at 0° C., separated and dried at 70° C. under reduced pressure to obtain 2.12 g of the expected product melting at 245° C.

EXAMPLE 8

(13aRS, trans) (±) 2,3,5,6,13a,13b-hexahydro indolo [3,2,1-de] [1,4] oxazino [2,3,4,-ij] [1,5] naphthyridine fumarate Using the procedure of Example 7, 4.3 g of the mixture of the hydroxylated epimers of Example 5 were reacted to obtain 3.4 g of product in the form of a base melting at 158° C. to 169° C. 1.3 g of this product were dissolved in 50 ml of ethyl acetate and 0.600 g of fumaric acid were added all at once. The mixture was dissolved in 75 ml of boiling ethyl acetate and the mixture was cooled to −50° C. and stood for one hour at this temperature, then was separated, washed with iced ethyl acetate and dried to obtain 1.2 g of the expected acid fumarate melting at 183° C. to 186° C.

EXAMPLE 9

[13aRS,trans) (±) 2,3,5,6,12,13,13a,13b-octahydro indolo [3,2,1-de] [1,4] oxazino [2,3,4-ij] [1,5] naphthyridine fumarate 3.8 g of the product of Example 8 were dissolved in 190 ml of ethanol and 0.380 g of 82% platinum dioxide were added. Hydrogenation was carried out for 90 minutes and after filtering, the filtrate was evaporated to obtain 3.9 g of saturated product melting at 125° C. 2 g of this product were dissolved in 60 ml of an ethyl acetate - isopropyl ether mixture (1-1) and after filtering, 0.460 g of fumaric acid were added to the filtrate. The mixture was dissolved in 20 ml of boiling ethanol and the mixture was cooled to −15° C. to −10° C. for one hour, then filtered, washed with an iced ethyl acetate -isopropyl ether mixture and dried to obtain 1.37 g of the expected acid fumarate melting at 210° C.

NMR Spectrum of the base 400 MHz CDCl$_3$ trans junction, 3.50 (d,d,d J=4.5–9–11.5): axial CH-O, 3.08: axial CH-N, 4.34 (m) 3.80 (m): indole CH$_2$-N, 3.98 (dt) 4.06 (m): morpholine CH$_2$-O.

EXAMPLE 10

(cis dl) (13aRS,cis) (±) 2,3,5,6,12,13,13a,13b-octahydro indolo [3,2,1-de] [1,4] oxazino [2,3,4-ij] [1,5] naphthyridine hemifumarate 3.30 g of the product of Example 7 were dissolved in 200 ml of ethanol and 0.33 g of 82% platinim oxide were added. Hydrogenation was carried out for 75 minutes and after filtering, the filtrate was concentrated to 100 ml. 0.755 g of fumaric acid dissolved in 25 ml of boiling ethanol were added and the mixture was stirred for one hour at ambient temperature and separated to obtain 3.30 g of the expected hemifumarate melting at 240° C.

NMR Spectrum CDCl₃ ppm on base, 4.08 (cis junction): CH-N and CH-O, 4.12 (m): indole CH$_2$N, 7.12 (dt) 7.19 (dt): indole H$_5$ and H$_6$, 7.32 (d) 7.50 (d): indole H$_4$ and H$_7$, 2.1 to 3.9: other protons.

EXAMPLE 11

(16α) (±) 11-methoxy 20,21-dinor 17-oxaeburnamenin-14 (15H)-one acid maleate

STEP A: Ethyl [2-[(6-methoxy 1H-indol-3-yl)-ethyl]-amino]-acetate 18.3 of 1,8-diazabicyclo [5,4,0] undec-7-ene (DBU) were added to a suspension of 19 g of 6-methoxy tryptamine and 380 ml of tetrahydrofuran and 20 g of ethyl bromoacetate were added to the solution followed by stirring for 24 hours at ambient temperature. The insoluble part was filtered off and the filtrate was concentrated to dryness under reduced pressure. The 20 g of residue were chromatographed on silica (eluent: methylene chloride - methanol 95-5) to obtain 19 g of the sought product melting at approx. 60° C.

IR Spectrum (CHCl₃), indole NH: 3479 cm$^{-1}$, NH-CH$_2$: 3322 cm$^{-1}$, >C=O: 1734 cm$^{-1}$.

STEP B: 2-[2-[6-methoxy 1H-indol-3-yl)-ethyl]-amino]-ethanol 245 ml of a 2.3M solution of diethylhydride of sodium and aluminium in toluene were added at 20° C.±3° C. to a solution of 20 g of the product of Step A in 400 ml of tetrahydrofuran followed by stirring for 2 hours at ambient temperature. 200 ml of tetrahydrofuran with 20% of water were then added slowly at 20° C.±3° C., with stirring for 90 minutes at ambient temperature. The insoluble part was filtered off and washed twice with 400 ml of tetrahydrofuran. The filtrate and the washings were evaporated to dryness under reduced pressure and the residue was triturated in 200 ml of isopropyl ether to obtain 13.5 g of the sought product melting at 123° C.

IR Spectrum (CHCl₃), OH: 3610 cm$^{-1}$, indole NH: 3480 cm$^{-1}$, aromatic: 1630, 1580, 1558, 1501 cm$^{-1}$.

STEP C: Methyl [4-[2-(6-methoxy-1-H-indol-3-yl)-ethyl]-3-oxo-2-morpholinyl]-acetate A solution of 39.5 g of potassium carbonate in 80 ml of water and 0.67 g of tetrabutylammonium bromide were added to a suspension of 13.4 g of the amino alcohol of Step B and 166 ml of chloroform. 0.063 ml of 2-bromo-4-methyl-butanedioic acid chloride (preparation 1) in solution in 165 ml of chloroform were introduced over 45 minutes at ambient temperature followed by stirring for 20 hours at ambient temperature. The phases were separated by decanting and the aqueous phase was extracted twice with 100 ml of chloroform. The organic fractions were washed with water and concentrated to dryness under reduced pressure. The 25 g of residue were dissolved in 250 ml of tetrahydrofuran and 25 g of potassium carbonate were added. The mixture was refluxed for 16 hours with stirring. The insoluble part was filtered off and washed three times with 100 ml of tetrahydrofuran. The filtrate and the washings were evaporated to dryness under reduced pressure. The 25 g of residue were chromatographed on silica (eluent: ethyl acetate - methylene chloride 8-2) to obtain 16 g of the sought product.

IR Spectrum (CHCl₃), carbonyl: 1735 cm$^{-1}$ ester, 1649 cm$^{-1}$, CH$_3$ of the COOCH$_3$: 1439 cm$^{-1}$, aromatic: 1571, 1558, 1500, 1493 cm$^{-1}$, OCH$_3$: 2835 cm$^{-1}$.

STEP D: (16) (±) 11-methoxy-20,21-dinor 17-oxaeburnamenin-14-(15H)-one 14 ml of phosphorus oxychloride were added to a solution of 14 g of the product of Step C in 280 ml of dioxane and the mixture was stirred for 3 hours at 80° C., then evaporated to dryness under reduced pressure. The residue was taken up in 140 ml of acetone and 1.4 g of ascorbic acid were added. The mixture was heated to 45° C. to 50° C. and 140 ml of concentrated ammonia were added. The mixture was stirred for 90 minutes at 50° C. and 560 ml of water and ice were added to the reaction mixture. The mixture was stirred for 90 minutes and the solid precipitate was isolated by separation and was washed with iced water. The moist product was taken up in 280 ml of acetic acid and was reduced by the addition of 14 g of sodium borohydride at 15° C. ±5° C. with stirring for one hour. The medium was alkalized at 15° C. ±5° C. by the addition of concentrated ammonium. The suspension was filtered and the 10 g of crude product were chromatographed on silica (eluent: methylene chloride - methanol 95-5), then once again with ethyl acetate only to obtain 6 g of the expected product melting at 164° C.

IR Spectrum (CHCl₃), >=0: 1706 cm$^{-1}$, aromatic: 1663, 1616, 1575, 1487 cm$^{-1}$, Bohlmann bands.

STEP E: (16α) (±) 11-methoxy-20,21-dinor-17-oxaeburnamenin-14-(15H)-one acid maleate 0.800 g of the product of Step D were dissolved in 20 ml of boiling ethyl acetate and 0.310 g of maleic acid in solution in 10 ml of boiling ethyl acetate were added. The mixture was stirred for one hour at 0° C. followed by filtration to obtain 0.910 g of the expected maleate melting at 188° C.

Analysis: C$_{17}$H$_{18}$N$_2$O$_3$, C$_4$H$_4$O$_4$, Calculated: % C 60.86, % H 5.35, % N 6.76: Found: 60.8, 5.2, 6.6.

Preparation: 2-bromo-4-methyl-butanedioic acid chloride 14.6 ml of thionyl chloride were added to a solution of 13.3 g of 2-bromo-4-methyl-butanedioic acid in 133 ml of chloroform and the mixture was refluxed for one hour with stirring. The excess chloroform and thionyl chloride were distilled off under reduced pressure to obtain the expected acid chloride which was used as in Step C.

EXAMPLE 12

(14 α, 16 α) (±) 14,15-dihydro-11-methoxy-20,21-dinor-17-oxaeburnamenin-14-ol 11.2 ml of 2.3M solution of sodium diethylaluminium hydride in toluene were added over 15 minutes at 0° C. to +5° C. to a solution of 1.58 g of the product of Step D of Example 11 in 30 ml of tetrahydrofuran. The mixture was stirred for 90 minutes at 0° C. to +5° C. and then was hydrolyzed by the addition of 20 ml of tetrahydrofuran with 20% of water. After stirring for 2 hours at ambient temperature, the insoluble part was filtered off and the filtrate was evaporated to dryness under reduced pressure. The residue was chromatographed on silica (eluent: methylene chloride - acetone 1-1) to obtain 0.600 g (isomer B, equatorial OH) melting at 202° C. and 0.440 g (expected isomer A, axial OH) melting at 220° C.

Analysis: $C_{17}H_{20}N_2O_3$, Calculated: % C 67.98, % H 6.71, % N 9.33: Found: 67.9, 6.9, 9.2.

EXAMPLE 13

(16α) (±) 11-methoxy-20,21-dinor-17-oxaeburnamenine acid maleate

STEP A: (16α) (±) 11-methoxy-20,21-dinor-17-oxaeburnamenine 30 mg of p-toluene sulfonic acid were added to a solution of 0.58 g of product B of Example 12 (equatorial OH) in 20 ml of toluene, and the mixture was refluxed over night and after distilling to dryness under reduced pressure, the residue was chromatographed on silica (eluent: ethyl acetate - methylene chloride 8-2) to obtain 0.43 g of the sought product melting at 104° C.

IR Spectrum (CHCl₃), OH: None, —C═C—: 1663 cm⁻¹, aromatic: 1620, 1610, 1568, 1486 cm⁻¹, Bohlmann bands. STEP B: (16) (±) 11-methoxy-20,21-dinor-17-oxaeburnamenine acid 0.38 g of the product of Step A were dissolved in 10 ml of ethyl acetate, and a solution of 0.156 g of maleic acid in 5 ml of boiling ethyl acetate was added. The mixture was stirred for 30 minutes at ambient temperature and then filtered. The 0.53 g of crude product was crystallized, first from 100 volumes of ethyl acetate and a second time from 100 volumes of acetone to obtain 0.32 g of the expected product melting at 185° C.

Analysis: $C_{21}H_{22}N_2O_6$, Calculated: % C 63.31, % H 5.56, % N 7.03: Found: 63.2, 5.7, 6.9.

EXAMPLE 14

(16a) (±) 10-methyl-20,21-dinor-17-oxaeburnamenin-14-(15H)-one acid maleate

STEP A: Ethyl [2-[(5-methyl-1H-indol-3-yl)-ethyl]-amino]-acetate

Using the procedure of Step A of Example 11, 21.5 g of 5-methyl-tryptamione were reacted for 24 hours at reflux instead of 24 hours at ambient temperature to obtain 13.2 g of the sought product.

IR Spectrum (CHCl₃), >0 ester: 1734 cm⁻¹, indole NH: 3481 cm⁻¹, aromatic: 1626, 1583, 1580 cm⁻¹.

STEP B: 2-[2-[(5-methyl-1H-indol-3-yl)-ethyl]-amino]-ethanol 300 ml of lithium triethylborohylride in 1M solution of tetrahydrofuran were added over 20 minutes at 0 C. to 5 C. to a solution of 13 g of the product of Step A in 260 ml of tetrahydrofurna. The mixture was stirred for 2 hours at ambient temperature, then was hydrolyzed for one hour after the addition of 100 ml of tetrahydrofuran with 20% of water. After evaporation to dryness under reduced pressure, the residue was taken up in 250 ml of ethyl acetate and 125 ml of water. The pH was adjusted to 7 with N hydrochloric acid and after decanting, the aqueous phase was extracted twice with 100 ml of ethyl acetate and concentrated to dryness under reduced pressure. The 10 g of residue were chromatographed on silica (eluent: methylene chloride - methanol - triethylamine 8-1-1) to obtain 4.4 g of the expected product.

| NMR Spectrum 60 MHz in H₃ CDCl₃ ppm | |
|---|---|
| 1.49 | 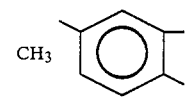 |
| 1.60 to 1.90 | N—C$\underline{H}_2$—CH₂—O |
| 2.20 (m) | N—CH₂—C$\underline{H}_2$—O |
| 1.79 | —C—C$\underline{H}_2$—C$\underline{H}_2$—N |
| 4.10 to 4.50 | aromatic |
| 5.09 | mobile proton. |

STEP C: Methyl [4-[2-(5-methyl-1H-indol-3-yl)-ethyl]-3-oxo-2-morpholinyl]-acetate A solution of 2-bromo-4-methyl butanedioic acid chloride (prepared as indicated in preparation 1 from 4.25 g of acid) in 20 ml of chloroform was introduced over 10 minutes at ambient temperature into mixture of 4 g of the product of Step B, 80 ml of chloroform and 25 g of potassium carbonate in 40 ml of water. The mixture was stirred for 18 hours, decanted, extracted with chloroform and evaporated to dryness under reduced pressure. 7 g of residue were dissolved in 70 ml of tetrahydrofuran and 7 g of potassium carbonate were added. The mixture was stirred for 16 hours at reflux and the insoluble part was filtered off. The filtrate was concentrated to dryness under reduced pressure and the 7 g of residue were chromatographed on silica (eluent: ethyl acetate - methylene chloride 8-2) to obtain 4 g of the sought product melting at 138° C.

| IR Spectrum (CHCl₃) | |
|---|---|
| indole NH | 3480 cm⁻¹ |
|  | 1649 cm⁻¹ |
|  | 1736 cm⁻¹ |
| methyl of the ester | 1439 cm⁻¹ |

STEP D: (16) (±) 10-methyl-20,21-dinor-17-oxaeburnamenin-14 (15H)-one

Using the procedure of Step D of Example 11, 2.25 g of the product of Step C and pure phosphorus oxychloride were reacted to obtain 1.53 g of the expected product melting at 196° C.

IR Spectrum (CHCl₃), indole NH: undetected, >C═0: 1707 cm⁻¹, aromatic: 1656 cm⁻¹, Bohlmann bands.

STEP E: (16α) (±) 10-methyl-20,21-dinor-17-oxaeburnamenin-14(15H)-one acid maleate Using the procedure of Step E of Example 11, 0.5 g of the product of Step D were reacted to obtain 0.62 g of the sought product melting at 200° C.

Analysis: $C_{21}H_{22}N_2O_6$, Calculated: % C 63.31, % H 5.56, % N 7.03: Found: 63.6, 5.5, 7.0.

EXAMPLE 15

(16α) (±) 10-methyl-20,21-dinor-17-oxaeburnamenin maleate

STEP A: (16α) (±) 14,15-dihydro-10-methyl-20,21-dinor-17-oxaeburnamenin-14-ol 3.9 ml of a 2.63M solution of sodium aluminum diethyldihydroaluminate in toluene were added over 10 minutes at ambient temperature to a solution of 1.3 g of the product of Step D of Example 14 in 25 ml of tetrahydrofuran. The mixture was stirred for one hour at ambient temperature and then 6 ml of tetrahydrofuran with 25% of water were added followed by stirring for one hour. The insoluble part was filtered off and the filtrate was evaporated to dryness under reduced pressure to obtain 1.3 g of a mixture of 2 epimers, axial and equatorial OH. The crude product was used as is for the following step.

STEP B: (16α) (±) 10-methyl-20,21-dinor-17-oxaeburnamenine acid maleate 20 mg of p-toluenesulfonic acid were added to a solution of 0.39 g of the isomer mixture of Step A in 10 ml of toluene followed by reflux for 3 hours with stirring. The solvent was distilled off under reduced pressure and the residue was chromatographed on siica (eluent: methylene chloride - acetone 1-1) to obtain 0.22 g of the sought product in the form of a base melting at 130° C.

Salification

A solution of 52 mg of maleic acid in 2 ml of ethyl acetate was added to a solution of 0.12 g of the said base in 5 ml of ethyl acetate and the mixture was stirred for one hour, then filtered to obtain 90 mg of the expected product melting at 166° C.

Analysis: $C_{21}H_{22}N_2O_5$, Calculated: % C 65.96, % H 5.80, % N 7.32: Found: 65.7, 5.8, 7.2.

EXAMPLE 16

Pharmaceutical composition

Tablets were prepared containing 50 mg of the product of Example 1 and sufficient excipient of lactose, talc, starch and magnesium stearate for a final weight of 350 mg.

PHARMACOLOGICAL DATA

A. Analgesic activity: hot-plate test

Female mice weighing 22 to 24 g were individually on a copper plate kept at 56° C. and the reaction to the pain was shown by the licking of the front paws of the animal. The time of this reaction was noted and only the mice reacting in less than 8 seconds were retained. The animals were divided into equal groups and treated with the product under test, administered orally, one group only received the medium. The time of reaction to the pain was again measured 30 to 60 minutes after treatment. The percentage of increase in the time of reaction was measured in minutes and the following results were obtained.

| Controls | | +21 |
|---|---|---|
| Product of Example 1 | 50 mg/kg | +80 |
| | 100 mg/kg | +107 |
| Controls | | +24 |
| Product of Example 9 | 50 mg/kg | +17 |
| | 100 mg/kg | +86 |

B. Asphyxic anoxia

The test was carried out on male Sprague Dawley rats (Charles River) anaesthetized with ethyl ether, immobilized (d. tubecurarine 1 mg/kg I.V.) and artificially ventilated with air. The electrocorticogram (ECOG) and the arterial pressure were recorded and the rectal temperature was kept at about 36° C. and the amount of carbon dioxide in the blood between 35 and 40 torr. The products were administered intravenously in a volume of 1 ml/kg 3 minutes before asphyxia obtained by stopping the artifical respiration. The latency time of the disappearance of the ECOG was measured. At 10 mg/kg, the products of Examples 1 and 6 increased the latency time of the disappearance of the ECOG by 23% and 34% respectively.

Various modifications of the products and method of the invention may be made without departing from the spirit or scope thereof and it should be understood that the invention is intended to be limited only as defined in the appended claims.

What we claim is:

1. A compound selected from the group consisting of all possible racemic or optically active forms of compounds of the formula

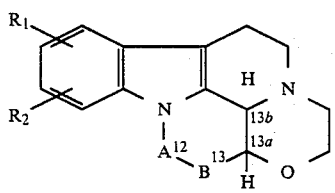

wherein $R_1$ and $R_2$ are individually selected from the group consisting of hydrogen, halogen alkyl and alkoxy of 1 to 5 carbon atoms, -OH, -$CF_3$ and -$NO_2$ and

is selected from the group consisting of

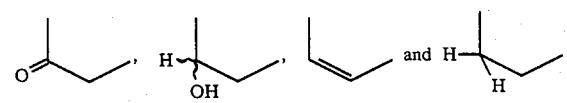

and their non-toxic, pharmaceutically acceptable acid addition salts.

2. A compound of claim 1 wherein $R_1$ and $R_2$ are individually selected from the group consisting of hydrogen, methyl, ethyl, methoxy, ethoxy, chlorine, -OH, -CF₃ and -NO₂.

3. A compound of claim 1 wherein

is selected from the group consisting of

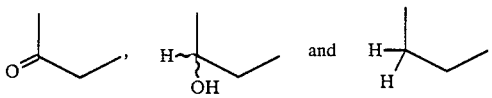

4. A compound of claim 1 selected from the group consisting of [12RS (12α, 13aα, 13bβ)] (±) 2,3,5,6,12,13,13a,13b-octahydro indolo [3,2,1-de] [1,4] oxazino [2,3,4,-ij] [1,5] naphthyridin-12-ol and its non-toxic, pharmaceutically acceptable acid addition salts.

5. A compound of claim 1 selected from the group consisting of [12RS 12aα, 13aβ, 13bα)] (±) 2,3,5,6,12,13,13a,13b-octahydro indolo [3,2,1-de] [1,4] oxazino [2,3,4-ij] [1,5] naphthyridin-12-ol and its non-toxic, pharmaceutically acceptable acid addition salts.

6. A compound of claim 1 selected from the group consisting of (13aRS-trans) (±) 2,3,5,6,12,13,13a,13b-octahydro indolo [3,2,1-de] [1,4] oxazino [2,3,4-ij] [1,5] naphthyridine and its non-toxic, pharmaceutically acceptable acid addition salts.

7. A compound of claim 1 selected from the group consisting of (13aRS-cis) (±) 2,3,5,6,13a,13b-hexahydro indolo [3,2,1-de] [1,4] oxazino [2,3,4-ij] [1,5] naphthyridine-12 (13H)-one and its non-toxic, pharmaceutically acceptable acid addition salts.

8. An analgesic composition comprising an analgesically effective amount of at least one compound of claim 1 and an excipient.

9. A composition of claim 8 wherein R₁ and R₂ are individually selected from the group consisting of hydrogen, methyl, ethyl, methoxy, ethoxy, chlorine, -OH, -CF₃ and -NO₂.

10. A composition of claim 8 wherein

is selected from the group consisting of

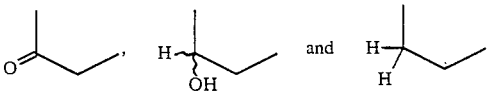

11. A composition of claim 8 wherein the active compound is selected from the group consisting of [12RS (12, 13aα, 13bβ)] (±) 2,3,5,6,12,13,13a,13b-octahydro indolo [3,2,1-de] [1,4] oxazino [2,3,4,-ij] [1,5] naphthyridin-12-ol and its non-toxic, pharmaceutically acceptable acid addition salts.

12. A composition of claim 8 wherein the active compound is selected from the group consisting of [12RS 12a, 13aβ, 13bα)] (±) 2,3,5,6,12,13,13a,13b-octahydro indolo [3,2,1-de] [1,4] oxazino [2,3,4-ij] [1,5] naphthyridin-12-ol and its non-toxic, pharmaceutically acceptable acid addition salts.

13. A composition of claim 8 wherein the active compound is selected from the group consisting of (13aRS-trans) (±) 2,3,5,6,12,13,13a,13b-octahydro indolo [3,2,1-de] [1,4] oxazino [2,3,4-ij] [1,5] naphthyridine and its non-toxic, pharmaceutically acceptable acid addition salts.

14. A composition of claim 8 wherein the active compound is selected from the group consisting of (13aRS-cis) (±) 2,3,5,6,13a,13b-hexahydro indolo [3,2,1-de] [1,4] oxazino [2,3,4-ij] [1,5] naphthyridine-12 (13H)-one and its non-toxic, pharmaceutically acceptable acid addition salts.

15. A method of relieving pain in warm-blooded animals comprising administering to warm-blooded animals an analgesically effective amount of at least one compound of claim 1.

16. A method of claim 15 wherein R₁ and R₂ are individually selected from the group consisting of hydrogen, methyl, ethyl, methoxy, ethoxy, chlorine, -OH, -CF₃ and -NO₂.

17. A method of claim 16 wherein

is selected from the group consisting of

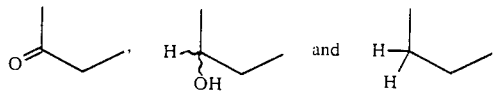

18. A method of claim 15 wherein the active compound is selected from the group consisting of [12RS (12α, 13aα, 13bβ)] (±) 2,3,5,6,12,13,13a,13b-octahydro indolo [3,2,1-de] [1,4] oxazino [2,3,4,-ij] [1,5] naphthyridin-12-ol and its non-toxic, pharmaceutically acceptable acid addition salts.

19. A method of claim 15 wherein the active compound is selected from the group consisting of [12RS 12aα, 13aβ, 13bα)] (±) 2,3,5,6,12,13,13a,13b-octahydro indolo [3,2,1-de] [1,4] oxazino [2,3,4-ij] [1,5] naphthyridin-12-ol and its non-toxic, pharmaceutically acceptable acid addition salts.

20. A method of claim 15 wherein the active compound is selected from the group consisting of (13aRS-trans) (±) 2,3,5,6,12,13,13a,13b-octahydro indolo [3,2,1-de] [1,4] oxazino [2,3,4-ij] [1,5] naphthyridine and its non-toxic, pharmaceutically acceptable acid addition salts.

21. A method of claim 15 wherein the active compound is selected from the group consisting of (13aRS-cis) (±) 2,3,5,6,13a,13b-hexahydro indolo [3,2,1-de] [1,4] oxazino [2,3,4-ij] [1,5] naphthyridine-12 (13H)-one and its non-toxic, pharmaceutically acceptable acid addition salts.

* * * * *